United States Patent [19]

Svendsen

[11] Patent Number: 4,629,695

[45] Date of Patent: Dec. 16, 1986

[54] PEPTIDE DERIVATIVES AND USE THEREOF AS SUBSTRATES FOR QUANTITATIVELY ASSAYING ENZYMES

[75] Inventor: Lars G. Svendsen, Reinach BL, Switzerland

[73] Assignee: Pentapharm A.G., Basel, Switzerland

[21] Appl. No.: 616,257

[22] Filed: Jun. 1, 1984

[30] Foreign Application Priority Data

Jun. 3, 1983 [CH] Switzerland ............... 3051/83
Jul. 5, 1984 [CH] Switzerland ............... 2214/84

[51] Int. Cl.$^4$ ............................................. C12Q 1/44
[52] U.S. Cl. ................................. 435/19; 260/998.2; 435/4; 530/331; 530/802
[58] Field of Search ............... 260/112.5 L, 998.2; 435/4, 18, 19; 530/331, 802

[56] References Cited

U.S. PATENT DOCUMENTS 4,217,269  8/1980  Cole .......................... 260/112.5 L
4,221,706  9/1980  Ali et al. .................... 260/112.5 L
4,279,810  7/1981  Claeson et al. ............. 260/112.5 L
4,379,764  4/1983  Fujii et al. ................. 260/112.5 L Primary Examiner—Sidney Marantz
Assistant Examiner—William J. Herald
Attorney, Agent, or Firm—Pennie & Edmonds

[57] ABSTRACT

Peptide derivatives of formula

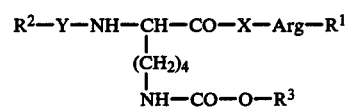

wherein $R^1$ represents a substituted amino group which is capable of being split off enzymatically with formation of a colored or fluorescent compound $R^1$-H. The said peptide derivatives are used for quantitatively assaying the enzyme $C_1$-esterase. The assaying is carried out by reacting a medium which contains $C_1$-esterase or in which the latter is formed or consumed with a peptide derivative as defined above and measuring photometrically, spectrophotometrically, fluorescence-spectrophotometrically or electrochemically the quantity of split product $R^1$-H released per time unit by the catalytic hydrolytic action of the said enzyme on the peptide derivative.

9 Claims, No Drawings

PEPTIDE DERIVATIVES AND USE THEREOF AS SUBSTRATES FOR QUANTITATIVELY ASSAYING ENZYMES

BACKGROUND

The present invention relates to new peptide derivatives which are easily split by certain enzymes, in particular by $C_1$-esterase. The said peptide derivatives are therefore useful as substrates for quantitatively assaying $C_1$-esterase in media which contain the said enzyme or in which the said enzyme is formed or consumed.

Human blood contains an active principle known under the name $C_1$-esterase proenzyme which is activated to the active enzyme $C_1$-esterase by the action of the combination of an antibody and an antigen. This enzyme activates in a cascade-like manner further proenzymes to active enzymes in the complement system. In turn, these activated enzymes cause lysis of the cell membranes of bacteria or dead erythrocytes and, consequently, play an important part in the immunological defence. Plasma also contains an important inhibitor which inhibits $C_1$-esterase and is called $C_1$-esterase inhibitor. In inflammatory processes $C_1$-esterase is activated whereby the complement system is activated more or less rapidly depending on the $C_1$-esterase inhibitor level in the blood. From a clinical point of view it is desirable to determine the $C_1$-esterase level as well as the $C_1$-esterase inhibitor level in blood. At present these determinations are carried out by cumbersome and inaccurate immunological and titrimetric methods (cf. W. J. Canady et al., Immunochemistry 1976, vol. 13, 229–233, and D. Ogston et al., Thrombosis Research, vol. 9, p. 217–222 (1976)).

SUMMARY

It was found that the determination of $C_1$-esterase can be performed substantially more rapidly and more accurately if certain simple peptide derivatives, which are the subject matter of the present invention, are used as substrates.

The present invention relates to peptide derivatives having the formula

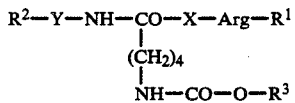

wherein
$R^1$ represents a chromogenic amino group which is substituted with an aromatic or heterocyclic radical and which is capable of being split off by enzymatic hydrolysis with formation of a colored or fluorescent compound,
$R^2$ represents hydrogen or
  (a) a straight or branched alkanoyl group having 2 to 6 carbon atoms,
  (b) a cyclohexylcarbonyl group,
  (c) an ω-carboxyl, ω-methoxycarbonyl or ω-ethoxycarbonylalkanoyl group having 2 to 4 carbon atoms in the alkanoyl,
  (d) a straight or branched alkoxycarbonyl group having 1 to 4 carbon atoms in the alkoxy,
  (e) an alkylsulfonyl group having 1 to 2 carbon atoms in the alkyl or a phenyl- or p-toluyl-sulfonyl group,
  (f) an unsubstituted or substituted benzoyl group, or
  (g) a benzyloxycarbonyl group the nucleus of which is unsubstituted or substituted,
$R^3$ represents a benzyl group the nucleus of which is unsubstituted or substituted,
X represents a glycyl or alanyl group, and
Y represents a single bond or a group of formula

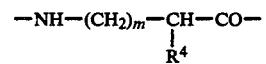

wherein $R^4$ represents a benzyl, phenyl, cyclohexyl, cyclohexylmethyl, 4-hydroxybenzyl or 4-hydroxycyclohexylmethyl group and m represents number zero, the amino acid represented by Y having L- or D-configuration, or $R^4$ represents hydrogen and m represents number zero, 1 or 2, and salts thereof with mineral or organic acids.

Furthermore, the invention relates to a method for quantitatively assaying the enzyme $C_1$-esterase in a medium which contains the said enzyme or in which the said enzyme is formed or consumed, more particularly in human blood plasma, which comprises reacting the said medium with a peptide derivative as disclosed above and measuring photometrically, spectrophotometrically, fluorescence-spectrophotometrically or electrochemically the quantity of split product $R^1$-H released per time unit by the enzymatic hydrolytic action of the said enzyme on the said peptide derivative.

DETAILED DESCRIPTION

In the general formula of the peptide derivatives according to the invention $R^1$ can represent, e.g., a p-nitrophenylamino-, 1- or 2-naphthylamino-, 4-methoxy-2-naphthylamino-, 4-methyl-7-coumarylamino- or 1,3-di(methoxycarbonyl)-5-phenylamino group.

$R^3$ can represent, e.g., a benzyl-, 4-methyl-benzyl-, 4-methoxybenzyl- or 2-, 3- or 4-chlorobenzyl group.

Among the peptide derivatives of the general formula disclosed above those in which $R^2$ is an alkanoyl group having 2 to 6 carbon atoms or an alkoxycarbonyl group having 1 to 4 carbon atoms, Y is a single bond and $R^3$ is a benzyl group and $R^1$ and X have the meaning defined above, are particularly sensitive to $C_1$-esterase.

Examples of peptide derivatives of the formula disclosed above include the following compounds: BOC-Lys(ε-Cbo)-Gly-Arg-pNA.AcOH, 2AcOH.H-Lys(ε-Cbo)-Gly-Arg-pNA, Ac-Lys(ε-Cbo)-Gly-Arg-pNA.AcOH, CH$_3$OCO-Lys(ε-Cbo)-Gly-Arg-pNA.AcOH, C$_2$H$_5$OCO-Lys(ε-Cbo)-Gly-Arg-pNA.AcOH, iso-ButOCO-Lys(ε-Cbo)-Gly-Arg-pNA.AcOH, CH$_3$CH$_2$CO-Lys(ε-Cbo)-Gly-Arg-pNA.AcOH, CH$_3$(CH$_2$)$_2$CO-Lys(ε-Cbo)-Gly-Arg-pNA.AcOH, CH$_3$CH$_2$OCO-CH$_2$-CO-Lys(ε-Cbo)-Gly-Arg-pNA.AcOH, BOC-Lys(ε-Cbo)-Ala-Arg-pNA.AcOH, H-Lys(ε-Cbo)-Ala-Arg-pNA.2CF$_3$COOH, Ac-Lys(ε-Cbo)-Ala-Arg-pNA.AcOH, CH$_3$O-CO-Lys(ε-Cbo)-Ala-Arg-pNA.AcOH, BOC-Gly-Lys(ε-Cbo)-Gly-Arg-pNA.AcOH, 2CF$_3$COOH.H-Gly-Lys(ε-Cbo)-Gly-Arg-pNA, CH$_3$O-CO-Gly-Lys(ε-Cbo)-Gly-Arg-pNA.AcOH and CH$_3$-CH$_2$-CO-Gly-Lys(ε-Cbo)-Gly-Arg-pNA.AcOH.

The peptide derivatives according to the invention can be prepared by the methods conventionally used in the peptide synthesis, for instance by the methods described hereinafter:

(1) The chromogenic group $R^1$ is attached to the carboxyl group of the C-terminal arginine, whilst its α-amino group is protected by a protecting group, e.g. a carbobenzoxy or tert.-butoxycarbonyl group, and the δ-guanidyl group of arginine is protected by protonation, e.g. with HCl, or nitration or tosylation. The C-terminal group $R^1$-serves also as a protective group during the step-wise building up of the peptide chain. The remaining protective groups can be removed selectively as needed in order to attach the next amino acid derivative until the desired peptide chain is completely built up. Finally, the remaining protective groups can be entirely removed without group $R^1$-being affected (cf. e.g. Miklos Bodansky et al., "Peptide Synthesis", Interscience Publishers, p. 163–165, 1966).

(2) In a first step the peptide chain is built up (according to Bodansky, loc.cit.) while the C-terminal carboxyl group of arginine is protected by a usual ester group, e.g. a methoxy, ethoxy or benzyloxy group. The ester groups can be removed by alkaline hydrolysis, except for the tert.-butoxy group which has to be removed selectively by means of trifluoroacetic acid. If the δ-guanidyl group of arginine is protonated, the ester group is removed by trypsin, no racemization taking place in this case. Thereafter, the chromogenic group $R^1$ is introduced. If the δ-guanidino group of arginine is protected by a nitro or tosyl group and the N-terminal α-amino group of the peptide derivative is protected by a carbobenzoxy group or a p-methyl, p-methoxy or p-chlorobenzyloxycarbonyl group, or a tert.-butoxy group, all these protective groups are removed simultaneously. The removal can be achieved by treating the protected peptide derivative with anhydrous HF at room temperature, and as a result all the above mentioned amino and δ-guanidino protective groups are removed. The removal can also be carried out by treatment with 2N HBr in glacial acetic acid at room temperature if the protected peptide derivative does not contain any nitro or tosyl group as protective groups.

In the following working examples the preparation of peptide derivatives of the invention is described in a detailed manner. Temperatures are indicated in centigrades.

The analyses of the eluates and products obtained according to the examples were carried out by thin layer chromatography using glass plates coated with silicon dioxide gel (Merck, F 254). The thin layer chromatograms were developed by means of the solvent system n-butanol/acetic acid/water (3:1:1).

The following abbreviations are used:
Ac=acetyl
Ac₂O=acetic anhydride
AcOH=acetic acid
Ala=L-alanine
β-Ala=β-alanine
Arg=L-arginine
BOC=tert.-butoxycarbonyl
γ-But=4-aminobutyric acid
Bz=benzoyl
Bz₂O=benzoic acid anhydride
CHA=L-3-cyclohexylalanine
CHG=L-2-cyclohexylglycine
D-CHG=D-2-cyclohexylglycine
CHT=L-3-(4-hydroxycyclohexyl)-alanine (tyrosine hydrogenated in the nucleus)
Cbo=carbobenzoxy
DMF=dimethylformamide
DPA=dimethyl 5-amido-isophthalate
Et=ethyl
EtO=ethoxy
Et₃N=triethylamine
Gly=glycine
HMPTA=N,N,N',N',N'',N''-hexylmethylphosphoric acid triamide
iso-BuO=iso-butoxy
Lys=L-lysine
MCA=7-amido-4-methylcoumarin
MeO=methoxy
MeOH=methanol
NA=naphthylamide
OpNP=p-nitrophenoxy
pNA=p-nitroanilide
Ph'Gly=L-2-phenylglycine
Phe=L-phenylalanine
D-Phe=D-phenylalanine
SS=solvent system
Suc=succinyl
THF=tetrahydrofuran
TLC=thin layer chromatography or chromatogram
Tos=p-toluenesulfonyl If no specific reference is made to the D-form, the amino acids have the L-configuration.

EXAMPLE 1

BOC-Lys(ε-Cbo)-Gly-Arg-pNA.AcOH

1a. Cbo-Arg-pNA.HCl

In a 250 ml three-necked flask 16.0 g (47 mM) of Cbo-Arg-OH.HCl, which had been dried in vacuo over $P_2O_5$, were dissolved in 90 ml of abs. HMPTA at 20° in the absence of humidity. To the resulting solution there was added at room temperature first a solution of 4.74 g (47 mM) of Et₃N in 10 ml of HMPTA and then portionwise 16.4 g (100 mM) of p-nitrophenyl isocyanate (100% excess). After a reaction time of 24 hours at 20° the major portion of HMPTA was removed by distillation in vacuo. The residue was extracted several times with 30% AcOH. The residue was discarded. The combined AcOH extracts were further purified by passing them through a column of "Sephadex G-15" (Trade Mark) equilibrated with 30% AcOH and eluted with 30% AcOH. The fraction of the AcOH eluate which was split by treatment with trypsin with release of p-nitroaniline was freeze-dried. There were thus obtained 12.6 g of an amorphous powder which was homogeneous in the SS as shown by TLC. Elementary analysis and calculation from the empirical formula $C_{20}H_{25}N_6O_5Cl$ gave the following values: C=51.29% (51.67%), H=5.48% (5.42%), N=17.92% (18.08%), Cl=7.50% (7.63%). The values within brackets have been calculated.

1b. 2HBr.H-Arg-pNA 4.65 g (10 mM) of compound 1a were treated, while stirring, with 40 ml of 2N HBr in glacial acetic acid for 45 min. at 20° in the absence of moisture. The amino acid derivative dissolved with $CO_2$ evolution. The reaction solution was added dropwise with vigorous stirring to 250 ml of absolute ether. This resulted in the precipitation of 2HBr.H-Arg-pNA. The ethereal phase was sucked off, whereupon the solid phase was washed 4 times with portions of 100 ml of abs. ether in order to remove benzyl bromide which had formed as a by-product as well as excess HBr and AcOH. The residue was dissolved in 50 ml of MeOH, the pH was adjusted to 4.5 by the addition of Et₃N, and the solution was concentrated to dryness in vacuo at 30°. The resulting product was dissolved in 75 ml of MeOH and passed through a column of "Sephadex" LH-20 (cross-linked dextran gel) equilibrated with MeOH. From a fraction of the eluate there were obtained 4.18 g (91.6% of the theory) of amorphous compound 1b which was homogeneous in the SS as shown by TLC. Elementary analysis and calculation from the empirical formula $C_{12}H_{20}N_6O_3Br_2$ gave the following values: C=31.15% (31.60%), H=4.35% (4.42%), N=18.84% (18.43%) and Br=34.81% (35.03%).

1c. Cbo-Gly-Arg-pNA.HBr 4.56 g (10 mM) of compound 1b were dissolved in 30 ml of freshly distilled DMF, and the solution was cooled to −10°. 1.40 ml (10 mM) of Et₃N were added to the solution, while stirring. The formed Et₃N.HBr was removed by filtration and washed with a small quantity of cold DMF. 3.65 g (11 mM) of Cbo-Gly-OpNP were added at −10° to the filtrate, while stirring, and the reaction was allowed to proceed for 2-3 hours in the absence of moisture, whereby the temperature of the reaction solution gradually reached about 20°. The solution was again cooled to −10° and buffered with 0.70 ml (5 mM) of Et₃N. The reaction solution was allowed to react for about 2 hours at −10° and for about 3 hours at room temperature. This procedure was repeated with 0.70 ml of Et₃N, and after 16 hours the reaction solution was concentrated to dryness in vacuo at 50°. The residue was dissolved in 75 ml of 50% AcOH and purified by gel filtration on a column of "Sephadex" G-15 equilibrated with 50% AcOH. The fraction of the AcOH eluate which was split by treatment with trypsin with release of p-nitroaniline was concentrated to dryness in vacuo at 40°. The residue was dissolved in 150 ml of MeOH and again concentrated to dryness. The resulting residue was dried in a vacuum desiccator at 60° over $P_2O_5$ to obtain 5.85 g (88.3% of the theory) of amorphous compound 1c which was homogeneous in the SS as shown by TLC. Elementary analysis and calculation from the empirical formula $C_{22}H_{28}N_7O_6Br$ gave the following values: C=46.33% (46.65%), H=5.04% (4.98%), N=17.88% (17.31%) and Br=14.20% (14.11%).

1d. 2HBr.H-Gly-Arg-pNA 4.56 g (8 mM) of compound 1c were treated, in the absence of humidity, while stirring, with 32 ml of 2N HBr in glacial acetic acid for 40 min. 20°. The dipeptide derivative gradually dissolved with $CO_2$ evolution. The reaction solution was added dropwise with vigorous stirring to 250 ml of abs. ether, and this resulted in the precipitation of 2HBr.H-Gly-Arg-pNA. The ethereal phase was sucked off, whereupon the solid phase was washed 4 times with portions of 100 ml of abs. ether in order to remove benzyl bromide which had formed as a by-product as well as excess HBr and AcOH. The residue was dissolved in 50 ml of MeOH. The pH was adjusted to 4.5 by means of Et₃N, and the solution was concentrated to dryness in vacuo at 30°. The resulting residue was dissolved in 50 ml of MeOH and purified on a column of "Sephadex" LH-20 equilibrated with MeOH. The fraction of the MeOH eluate which was split by treatment with trypsin with release of p-nitroaniline was concentrated to dryness in vacuo at 30°. The resulting residue was dried in a vacuum desiccator at 40° over $P_2O_5$ to obtain 3.78 g (92.1% of the theory) of amorphous compound 1d which was homogeneous in the SS as shown by TLC. Elementary analysis and calculation from the empirical formula $C_{14}H_{23}N_7O_4Br_2$ gave the following values: C=32.31% (32.77%), H=4.59% (4.52%), N=19.47% (19.11%) and Br=30.78% (31.14%).

1e. BOC-Lys(ε-Cbo)-Gly-Arg-pNA.HBr 2.57 g (5 mM) of compound 1d were dissolved in 20 ml of freshly distilled DMF, and the solution was cooled to −10°. 0.70 ml (5 mM) of Et₃N were added to the solution, while stirring. The formed Et₃N.HBr was removed by filtration and washed with a small quantity of cold DMF. 2.76 g (5.5 mM) of BOC-Lys(ε-Cbo)-OpNP were added at −10° to the filtrate, while stirring. The reaction mixture was allowed to react for 2-3 hours in the absence of moisture, whereby the temperature of the reaction solution gradually reached about 20°. The solution was again cooled to −10°, buffered with 0.35 ml (2.5 mM) of Et₃N and allowed to react for about 2 hours at −20° and for a further 3 hours at room temperature. This procedure was repeated with 0.35 ml of Et₃N, and after 16 hours the reaction solution was concentrated to dryness in vacuo at 50°. The residue was dissolved in 50 ml of 50% AcOH and purified by gel filtration on a column of "Sephadex" G-15 equilibrated with 50% AcOH. The fraction of the AcOH eluate which was split by treatment with trypsin with release of p-nitroaniline was concentrated to dryness in vacuo at 40°. The residue was dissolved in 100 ml of MeOH, and the solution was again concentrated to dryness. The resulting residue was dried in a vacuum desiccator at 60° over $P_2O_5$ to obtain 3.57 g (89.8% of the theory) of amorphous compound 1e which was homogeneous in the SS as shown by TLC. Elementary analysis and calculation from the empirical formula $C_{33}H_{48}N_9O_9Br$ gave the following values: C=49.38% (49.87%), H=6.00% (6.09%), N=16.03% (15.86%) and Br=9.85% (10.05%).

The amino acid analysis confirmed the presence of the expected amino acids in the correct proportions: Gly:1.00-Lys:0.99-Arg:0.97.

1f. BOC-Lys(ε-Cbo)-Gly-Arg-pNA.AcOH 7.95 g (10 mM) of BOC-Lys(ε-Cbo)-Gly-Arg-pNA.HBr (prepared according to paragraph 1e) were dissolved in 75 ml of 60% aqueous MeOH. The solution was poured on a column of "Amberlite" JRA-401 in the acetate form. The collumn was eluted by means of 60% aqueous MeOH, the HBr being replaced by AcOH by ion exchange. The eluate was concentrated to dryness in vacuo at 40°. After drying in the vacuum desiccator at 40° over $P_2O_5$ there were obtained 7.58 g of bromide-free BOC-Lys(ε-Cbo)-Gly-Arg-pNA.AcOH (97.9% of the theory).

Other salts with organic acids, e.g. formic acid, propionic acid, oxalic acid, tartaric acid, citric acid, lactic acid, benzoic acid, chlorobenzoic acid, salicylic acid or phthalic acid, can also be prepared from the above named tripeptide derivative according to the same method. The ion exchanger can be e.g. "Amberlite" JRA-401 in its hydrochloride form, and the desired acid salt form can be obtained by converting the said ion exchanger into the basic OH-form by treatment with caustic soda solution and then with a solution of a 1:1 mixture of the desired organic acid and its sodium salt in 60% aqueous MeOH.

EXAMPLE 2

BOC-Lys(ε-Cbo)-Gly-Arg-MCA-AcOH

2b. 2HBr.H-Arg-MCA 13.0 g (25.9 mM) of commercial Cbo-Arg-MCA.HCl were deblocked according to Example 1b by means of 104 ml (208 mM) of a solution of 2N HBr in glacial acetic acid. The dry residue was dissolved in 400 ml of MeOH and purified on a column of "Sephadex" LH-20. The fraction of the MeOH eluate which was split by treatment with trypsin with release of 4-methyl-7-amino-coumarin was concentrated to dryness in vacuo at 30°. The resulting residue was dried in a vacuum desiccator at 40° over $P_2O_5$ to obtain 11.2 g (87.7% of the theory) of amorphous compound 2b which was homogeneous in the SS as shown by TLC. Elementary analysis and calculation from the empirical formula $C_{16}H_{23}N_5O_3Br_2$ gave the following values: C=39.40% (38.96%), H=4.61% (4.70%), N=14.48% (14.20%) and Br=31.90% (32.40%).

2c. Cbo-Gly-Arg-MCA.HBr 4.93 g (10 mM) of compound 2b and 3.65 g (11 mM) of Cbo-Gly-OpNP were added to 75 ml of freshly distilled DMF. After cooling to −10°, there were added, while stirring, first 1.40 ml (10 mM) and then 0.70 ml (5 mM) of $Et_3N$. The mixture was allowed to react, in the absence of humidity, first for 3 hours at −10° and then for 4 hours at room temperature. The reaction solution was again cooled to −10°, buffered with 0.70 ml of $Et_3N$ and stirred overnight at 20°. The reaction mixture was concentrated to dryness in vacuo at 50°, and the residue was dissolved in 200 ml of 50% AcOH and purified on a column of "Sephadex" G-15. The fraction of the AcOH eluate which was split by treatment with trypsin with release of 4-methyl-7-aminocoumarin was concentrated to dryness in vacuo at 40°. The thus obtained residue was dried in a vacuum desiccator at 60° over $P_2O_5$ to yield 4.98 g (82.5% of the theory) of amorphous compound 2c which was homogeneous in the SS as shown by TLC. Elementary analysis and calculation from the empirical formula $C_{26}H_{31}N_6O_6Br$ gave the following values: C=51.48% (51.75%), H=5.24% (5.18%), N=13.70% (13.93%) and Br=13.14% (13.24%).

2d. 2HBr.H-Gly-Arg-MCA 4.83 g (8 mM) of compound 2c were deblocked according to Example 1d by means of 32 ml of 2N HBr in glacial acetic acid. The resulting crude product was dissolved in 100 ml of MeOH and purified on a column of "Sephadex" LH-20. The fraction of the MeOH eluate which was split by treatment with trypsin with release of 4-methyl-7-amino-coumarin was concentrated to dryness in vacuo at 30°. The resulting residue was dried in a vacuum desiccator at 40° over $P_2O_5$ to give 4.05 g (92.0% of the theory) of amorphous compound 2d which was homogeneous in the SS according to TLC. Elementary analysis and calculation from the empirical formula $C_{18}H_{26}N_6O_4Br_2$ gave the following values: C=39.02% (39.29%), H=4.78% (4.76%), N=15.39% (15.27%) and Br=28.72% (29.04%).

2e. BOC-Lys(ε-Cbo)-Gly-Arg-MCA.HBr 2.75 g (5 mM) of compound 2d were reacted with 2.76 g (5.5 mM) of BOC-Lys(ε-Cbo)-OpNP according to Example 1e. The resulting crude product was dissolved in 75 ml of 50% AcOH and purified on a column of "Sephadex" G-15. The fraction of the AcOH eluate which was split by treatment with trypsin with release of 4-methyl-7-amino-coumarin was concentrated to dryness in vacuo at 40°. The residue was dried in a vacuum desiccator at 60° over $P_2O_5$ to obtain 3.41 g (82.0% of the theory) of amorphous compound 2e which was homogeneous in the SS as shown by TLC. Elementary analysis and calculation from the empirical formula $C_{37}H_{51}N_8O_9Br$ gave the following values: C=53.13% (53.43%), H=6.24% (6.18%), N=13.76% (13.47%) and Br=9.45% (9.61%).

The amino acid analysis confirmed the presence of the expected amino acids in the correct proportions: Gly:1.00-Lys:1.02-Arg:0.98.

2f. BOC-Lys(ε-Cbo)-Gly-Arg-MCA.AcOH 8.32 g (10 mM) of compound 2e were converted into the corresponding acetate salt according to Example 1f. There were obtained 7.95 g (98.0% of the theory) of this product.

EXAMPLE 3

BOC-Lys(ε-Cbo)-Gly-Arg-DPA-AcOH

3a. Cbo-Arg-DPA.HCl 34.48 g (0.1 mole) of dried Cbo-Arg-OH.HCl were dissolved in a 1000 ml three-necked flask in a mixture of 150 ml of freshly distilled anhydrous DMF and 300 ml of abs. THF at 20°. To the solution, cooled to −10°, there were added, while stirring, 10.2 g (0.1 mole) of $Et_3N$ in the absence of humidity. Then a solution of 13.65 g (0.1 mole) of isobutyl chloroformate in 50 ml of THF was added dropwise within 20 minutes, whereby the reaction temperature was never allowed to exceed −5°. After an additional reaction time of 10 minutes at a temperature of −10° to −5° a solution of 20.92 g (0.1 mole) of dimethyl 5-amino-isophthalate in 75 ml of DMF was added dropwise within 30 minutes, whereby the reaction temperature was never allowed to exceed −5°. The reaction mixture was allowed to react for another hour at −5°. Then it was stirred overnight at 20° and subsequently cooled to −15° in order to let the $Et_3N.HCl$ crystallize. The formed $Et_3N.HCl$ was filtered off and washed with a small amount of cold DMF. The filtrate and the washing solution were concentrated to dryness in vacuo at 50°. The residue was dissolved in 1000 ml of 50% AcOH and purified by gel filtration on a column of "Sephadex" G-15 equilibrated with 50% AcOH. The fraction of the AcOH eluate which was split by treatment with trypsin with release of dimethyl 5-amino-isophthalate was concentrated to dryness in vacuo at 40°. The residue was dried in a vacuum desiccator at 50° over $P_2O_5$ to obtain 24.6 g (45.9% of the theory) of amorphous compound 3a which was homogeneous in the SS as shown by TLC. Elementary analysis and calculation from the empirical formula $C_{24}H_{30}N_5O_7Cl$ gave the following values: C=53.21% (53.78%), H=5.71% (5.64%), N=13.20% (13.07%) and Cl=6.52% (6.62%).

3b. 2HBr.H-Arg-DPA 21.44 g (40 mM) of compound 3a were deblocked according to Example 1b. After the usual treatment the resulting crude product was dissolved in 250 ml of MeOH and purified by gel filtration on a column of "Sephadex" LH-20. The fraction of the MeOH eluate which was split by treatment with trypsin with release of dimethyl 5-amino-isophthalate was concentrated to dryness in vacuo. The residue was dried in a vacuum desiccator at 40° over $P_2O_5$ to obtain 19.63 g (93.1% of the theory) of amorphous compound 3b which was homogeneous in the SS as shown by TLC. Elementary analysis and calculation from the empirical formula $C_{16}H_{25}N_5O_5Br_2$ gave the following values: C=36.82% (36.45%), H=4.67% (4.78%), N=13.45% (13.28%) and Br=29.85% (30.31%).

3c. Cbo-Gly-Arg-DPA.HBr 5.27 g (10 mM) of compound 3b were reacted according to Example 1c with 3.65 g (11 mM) of Cbo-Gly-OpNP. The crude product obtained after the usual treatment was dissolved in 200 ml of 50% AcOH and purified on a column of "Sephadex" G-15. The fraction of the AcOH eluate which was split by treatment with trypsin with release of dimethyl 5-amino-isophthalate was concentrated to dryness in vacuo at 40°. The residue was dried in a vacuum desiccator at 60° over $P_2O_5$ to give 5.29 g (83.0% of the theory) of amorphous compound 3c which was homogeneous in the SS as shown by TLC. Elementary analysis and calculation from the empirical formula $C_{26}H_{33}N_6O_8Br$ gave the following values: C=48.50% (48.99%), H=5.28% (5.22%), N=12.92% (13.18%) and Br=12.33% (12.53%).

3d. 2HBr.H-Gly-Arg-DPA 5.10 g (8 mM) of compound 3c were deblocked according to Example 1d by means of 32 ml of 2N HBr in glacial acetic acid. The crude product obtained after the usual treatment was dissolved in 100 ml of MeOH and purified on a column of "Sephadex" LH-20. The fraction of the MeOH eluate which was split by treatment with trypsin with release of dimethyl 5-amino-isophthalate was concentrated to dryness in vacuo at 30°. The residue was dried in a vacuum desiccator at 40° over $P_2O_5$ to give 4.25 g (90.9% of the theory) of amorphous compound 3d which was homogeneous in the SS as shown by TLC. Elementary analysis and calculation from the empirical formula $C_{18}H_{28}N_6O_6Br_2$ gave the following values: C=36.85% (37.00%), H=4.90% (4.83%), N=14.72% (14.38%) and Br=26.95% (27.35%).

3e. BOC-Lys($\epsilon$-Cbo)-Gly-Arg-DPA.HBr 2.92 g (5 mM) of compound 3d were reacted according to Example 1e with 2.76 g (5.5 mM) of BOC-Lys($\epsilon$-Cbo)-OpNP. The crude product obtained after the usual treatment was dissolved in 100 ml of 50% AcOH and purified on a column of "Sephadex" G-15. The fraction of the AcOH eluate which was split by treatment with trypsin with release of dimethyl 5-amino-isophthalate was concentrated to dryness in vacuo at 40°. The residue was dried in a vacuum desiccator at 60° over $P_2O_5$ to obtain 3.64 g (84.1% of the theory) of amorphous compound 3e which was homogeneous in the SS as shown by TLC. Elementary analysis and calculation from the empirical formula $C_{37}H_{53}N_8O_{11}Br$ gave the following values: C=51.05% (51.33%), H=6.25% (6.17%), N=13.26% (12.94%) and Br=9.10% (9.23%).

The amino acid analysis confirmed the presence of the expected amino acids in the correct proportions: Gly:1.00-Lys:1.00-Arg:0.97.

3f. BOC-Lys($\epsilon$-Cbo)-Gly-Arg-DPA.AcOH 8.66 g (10 mM) of compound 3e were converted into the corresponding acetate salt in accordance with Example 1f. There were obtained 8.24 g (97.5% of the theory) of this product.

EXAMPLE 4

BOC-Lys($\epsilon$-Cbo)-Ala-Arg-2-NA.AcOH

4b. 2HBr.H-Arg-2-NA 9.40 g (20 mM) of commercial Cbo-Arg-2-NA.HCl were deblocked according to Example 1b with a solution of 80 ml of 2N HBr in glacial acetic acid. The product obtained after the usual treatment was dissolved in 150 ml of MeOH and purified on a column of "Sephadex" LH-20. The fraction of the MeOH eluate which was split by treatment with trypsin with release of 2-naphthylamine was concentrated to dryness in vacuo at 30°. The residue was dried in a vacuum desiccator at 40° over $P_2O_5$ to obtain 8.60 g (93.2% of the theory) of amorphous compound 4b which was homogeneous in the SS as shown by TLC. Elementary analysis and calculation from the empirical formula $C_{16}H_{23}N_5OBr_2$ gave the following values: C=42.08% (41.67%), H=5.12% (5.03%), N=14.68% (15.19%) and Br=33.96% (34.65%).

4c. Cbo-Ala-Arg-2-NA.HBr 4.6 g (10 mM) of compound 4b were reacted according to Example 1c with 3.80 g (11 mM) of Cbo-Ala-OpNP. The crude product obtained after the usual treatment was dissolved in 150 ml of 50% AcOH and purified on a column of "Sephadex" G-15. The fraction of the AcOH eluate which was split by treatment with trypsin with release of 2-naphthylamine was concentrated to dryness in vacuo at 40°. The residue was dried in a vacuum desiccator at 60° over $P_2O_5$ to obtain 4.95 g (84.5% of the theory) of amorphous compound 4c which was homogeneous in the SS as shown by TLC. Elementary analysis and calculation from the empirical formula $C_{27}H_{33}N_6O_4Br$ gave the following values: C=55.72% (55.39%), H=6.73% (5.68%), N=14.68% (14.35%) and Br=13.42% (13.65%).

4d. 2HBr.H-Ala-Arg-2-NA 4.68 g (8 mM) of compound 4c were deblocked according to Example 1d by means of 28 ml of 2N HBr in glacial acetic acid. The crude product obtained after the usual treatment was dissolved in 100 ml of MeOH and purified on a column of "Sephadex" LH-20. The fraction of the MeOH eluate which was split by treatment with trypsin with release of 2-naphthylamine was concentrated to dryness in vacuo at 30°. The residue was dried in a vacuum desiccator at 40° over $P_2O_5$ to give 4.08 g (95.8% of the theory) of amorphous compound 4d which was homogeneous in the SS as shown by TLC. Elementary analysis and calculation from the empirical formula $C_{19}H_{28}N_6O_2Br_2$ gave the following values: C=43.9% (42.87%), H=5.32% (5.30%), N=16.02% (15.79%) and Br=29.68% (30.02%).

4e. BOC-Lys($\epsilon$-Cbo)-Ala-Arg-2NA.HBr 2.66 g (5 mM) of compound 4d were reacted according to Example 1e with 2.76 g (5.5 mM) of BOC-Lys($\epsilon$-Cbo)-OpNP. The crude product obtained after the usual treatment was dissolved in 100 ml of 50% AcOH and purified on a column of "Sephadex" G-15. The first main fraction of the AcOH eluate which was split by treatment with trypsin with release of 2-naphthylamine was concentrated to dryness in vacuo at 40° and dried in a vacuum desiccator at 60° over $P_2O_5$. There were thus obtained 3.45 g (84.8% of the theory) of amorphous compound 4e which was homogeneous in the SS as shown by TLC. Elementary analysis and calculation from the empirical formula $C_{38}H_{53}N_8O_7Br$ gave the following values: C=55.88% (56.08%), H=6.63% (6.56%), N=14.02% (13.77%) and Br=9.80% (9.82%).

The amino acid analysis confirmed the presence of the expected amino acids in the correct proportions: Ala:1.00-Lys:1.02-Arg:0.97.

4f. BOC-Lys($\epsilon$-Cbo)-Ala-Arg-2-NA.AcOH 8.14 g (10 mM) of compound 4e were converted into the corresponding acetate salt in accordance with Example 1f. There were obtained 7.65 g (96.5% of the theory) of this product.

EXAMPLE 5

BOC-Lys($\epsilon$-Cbo)-Ala-Arg-1-NA.AcOH

5a. Cbo-Arg-1-NA.HCl 3.45 g (10 mM) of well dried Cbo-Arg-OH.HCl were dissolved, in the absence of moisture, in 100 ml of dried HMPTA. The solution was cooled to −10°, whereupon 1.39 ml (10 mM) of $Et_3N$ and then a solution of 1.35 g (10 mM) of isobutyl chloroformate in 20 ml of HMPTA were added dropwise within 15 min., the temperature being kept between −10° and −5°. To the resulting solution there was then added dropwise a solution of 1.72 g (12 mM) of 1-naphthylamine in 15 ml of HMPTA, whereby the above mentioned temperature was being maintained. The reaction mixture was concentrated to dryness in vacuo at 80°. The residue was dissolved in 100 ml of MeOH and purified by gel filtration on a column of "Sephadex" LH-20 in MeOH. The fraction of the eluate which was split by treatment with trypsin with release of 1-naphthylamine was homogeneous in the TLC. This fraction was concentrated to dryness. There were thus obtained 2.82 g of amorphous compound 5a (60.1% of the theory). Elementary analysis and calculation from the empirical formula $C_{24}H_{28}N_5O_3Cl$ gave the following values: C=61.07% (61.33%), H=6.10% (6.01%), N=15.05% (14.90%) and Cl=7.38% (7.54%).

5b. 2HBr.H-Arg-1-NA 9.40 g (20 mM) of compound 5a were deblocked with a solution of 80 ml of 2N HBr in glacial acetic acid in accordance with Example 1b. The product obtained after the usual treatment was dissolved in 150 ml of MeOH and purified on a column of "Sephadex" LH-20. The fraction of the MeOH eluate which was split by treatment with trypsin with release of 1-naphthylamine was concentrated to dryness in vacuo at 30°. The residue was dried in a vacuum desiccator at 40° over $P_2O_5$ to obtain 8.40 g (90.8% of the theory) of amorphous compound 5b which was homogeneous in the SS as shown by TLC. Elementary analysis and calculation from the empirical formula $C_{16}H_{23}N_5OBr_2$ gave the following values: C=42.20% (41.67%), H=5.08% (5.03%), N=15.33% (15.19%) and Br=34.10% (34.65%).

5c. Cbo-Ala-Arg-1-NA.HBr 4.6 g (10 mM) of compound 5b were reacted according to Example 1c with 3.80 g (11 mM) of Cbo-Ala-OpNP. The crude product obtained after the usual treatment was dissolved in 150 ml of 50% AcOH and purified on a column of "Sephadex" G-15. The fraction of the AcOH eluate which was split by treatment with trypsin with release of 1-naphthylamine was concentrated to dryness in vacuo at 40°. The residue was dried in a vacuum desiccator at 60° over $P_2O_5$ to obtain 4.80 g (82.1% of the theory) of amorphous compound 5c which was homogeneous in the SS as shown by TLC. Elementary analysis and calculation from the empirical formula $C_{27}H_{33}N_6O_4Br$ gave the following values: C=55.62% (55.39%), H=6.70% (5.68%), N=14.63% (14.35%) and Br=13.35% (13.65%).

5d. 2HBr.H-Ala-Arg-1-NA 4.68 g (8 mM) of compound 5c were deblocked with 28 ml of 2N HBr in glacial acetic acid in accordance with Example 1d. The crude product obtained after the usual treatment was dissolved in 100 ml of MeOH and purified on a column of "Sephadex" LH-20. The fraction of the MeOH eluate which was split by treatment with trypsin with release of 1-naphthylamine was concentrated to dryness in vacuo at 30°. The residue was dried in a vacuum desiccator at 40° over $P_2O_5$ to obtain 3.85 g (90.3% of the theory) of amorphous compound 5d which was homogeneous in the SS as shown by TLC. Elementary analysis and calculation from the empirical formula $C_{19}H_{28}N_6O_2Br_2$ gave the following values: C=43.09% (42.87%), H=5.38% (5.30%), N=16.10% (15.79%) and Br=29.80% (30.02%).

5e. BOC-Lys($\epsilon$-Cbo)-Ala-Arg-1-NA.HBr 2.66 g (5 mM) of compound 5d were reacted with 2.76 g (5.5 mM) of BOC-Lys($\epsilon$-Cbo)-OpNP in accordance with Example 1e. The crude product obtained after the usual treatment was dissolved in 100 ml of 50% AcOH and purified on a column of "Sephadex" G-15. The first main fraction of the AcOH eluate which was split by treatment with trypsin with release of 1-naphthylamine was concentrated to dryness in vacuo at 40° and then dried in a vacuum desiccator at 60° over $P_2O_5$. There were thus obtained 3.46 g (85% of the theory) of amorphous compound 5e which was homogeneous in the SS as shown by TLC. Elementary analysis and calculation from the empirical formula $C_{38}H_{53}N_8O_7Br$ gave the following values: C=55.98% (56.08%), H=6.68% (6.56%), N=13.82% (13.77%) and Br=9.80% (9.82%).

The amino acid analysis confirmed the presence of the expected amino acids in the correct proportions: Ala:1.00-Lys:1.01-Arg:0.97.

5f. BOC-Lys($\epsilon$-Cbo)-Ala-Arg-1-NA.AcOH 8.14 g (10 mM) of compound 5e were converted into the corresponding acetate salt according to Example 1f. There were obtained 7.77 g (98.0% of the theory) of this product.

EXAMPLE 6

BOC-Lys($\epsilon$-Cbo)-Ala-Arg-4-MeO-2NA.HBr

6b. 2HBr.H-Arg-4-MeO-2-NA 10.0 g (20 mM) of commercial Cbo-Arg-4-MeO-2-NA.HCl were deblocked according to Example 1b by means of 80 ml of 2N HBr in glacial acetic acid. The crude product obtained after the usual treatment was dissolved in 150 ml of MeOH and purified on a column of "Sephadex" LH-20. The main fraction of the MeOH eluate which was split by treatment with trypsin with release of 4-methoxy-2-naphthylamine was concentrated to dryness in vacuo at 30°. The residue was dried in a vacuum desiccator at 40° over $P_2O_5$ to give 8.98 g (91.4% of the theory) of amorphous compound 6b which was homogeneous in the SS as shown by TLC. Elementary analysis and calculation from the empirical formula $C_{17}H_{25}N_5O_2Br_2$ gave the following values: C=41.22% (41.57%), H=5.19% (5.13%), N=14.40% (14.26%) and Br=32.01% (32.53%).

6c. Cbo-Ala-Arg-4-MeO-2-NA.HBr 4.91 g (10 mM) of compound 6b were reacted according to Example 1c with 3.80 g (11 mM) of Cbo-Ala-OpNP. The crude product obtained after the usual treatment was dissolved in 150 ml of 50% AcOH and purified on a column of "Sephadex" G-15. The first main fraction of the AcOH eluate which was split by treatment with trypsin with release of 4-methoxy-2-naphthylamine was concentrated to dryness in vacuo at 40°. The residue was dried in a vacuum desiccator at 60° over $P_2O_5$ to obtain 4.86 g (79.0% of the theory) of amorphous compound 6c which was homogeneous in the SS as shown by TLC. Elementary analysis and calculation from the empirical formula $C_{28}H_{35}N_6O_5Br$ gave the following values: C=54.38% (54.64%), H=5.81% (5.73%), N=13.93% (13.65%) and Br=12.75% (12.98%).

6d. 2HBr.H-Ala-Arg-4-MeO-2-NA 4.31 g (7 mM) of compound 6c were deblocked according to Example 1d with 28 ml of 2N HBr in glacial acetic acid. The crude product obtained after the usual treatment was dissolved in 100 ml of MeOH and purified on a column of "Sephadex" LH-20. The main fraction of the MeOH eluate which was split by treatment with trypsin with formation of 4-methoxy-2-naphthylamine was concentrated to dryness in vacuo at 30°. The residue was dried in a vacuum desiccator at 40° over $P_2O_5$ to obtain 3.74 g (95.0% of the theory) of amorphous compound 6d which was homogeneous in the SS as shown by TLC. Elementary analysis and calculation from the empirical formula $C_{20}H_{30}N_6O_3Br_2$ gave the following values: C=43.01% (42.72%), H=5.44% (5.38%), N=15.25% (14.95%) and Br=28.03% (28.42%).

6e. BOC-Lys($\epsilon$-Cbo)-Ala-Arg-4-MeO-2-NA.HBr 2.81 g (5 mM) of compound 6d were reacted according to Example 1e with 2.76 g (5.5 mM) of BOC-Lys($\epsilon$-Cbo)-OpNP. The crude product obtained after the usual treatment was dissolved in 125 ml of 50% AcOH and purified on a column of "Sephadex" G-15. The first main fraction of the AcOH eluate which was split by treatment with trypsin with release of 4-methoxy-2-naphthylamine was concentrated to dryness in vacuo at 40°. The residue was dried in a vacuum desiccator at 60° over $P_2O_5$ to give 3.31 g (78.5% of the theory) of amorphous compound 6e which was homogeneous in the SS as shown by TLC. Elementary analysis and calculation from the empirical formula $C_{39}H_{55}N_8O_8Br$ gave the following values: C=55.05% (55.51%), H=6.63% (6.57%), N=13.40% (13.28%) and Br=9.30% (9.47%).

6f. BOC-Lys($\epsilon$-Cbo)-Ala-Arg-4-MeO-2-NA.AcOH 8.44 g (10 mM) of compound 6e were converted into the corresponding acetate salt according to Example 1f. There were obtained 8.05 g (97.8% of the theory) of this product.

| Ex. | End products | Starting products | Method Yield % | Elementary analysis found % | calc. % | Amino acid analysis |
|---|---|---|---|---|---|---|
| 7 | H—Lys($\epsilon$-Cbo)—Gly—Arg—pNA.2CF$_3$COOH $C_{32}H_{41}N_9O_{11}F_6$ | 1e (100 mmoles) CF$_3$COOH (115 ml) | Ex. 1d 94.6 | C 45.48 H 5.01 N 15.12 | 45.66 4.91 14.98 | Gly:Lys:Arg 1.00:1.02:0.98 |
| 8 | Ac—Lys($\epsilon$-Cbo)—Gly—Arg—pNA.AcOH $C_{32}H_{45}N_9O_{10}$ | 7 (10 mmoles) Ac$_2$O (15 mmoles) | Ex. 1e and 1f 80.8 | C 53.62 H 6.38 N 17.80 | 53.70 6.34 17.61 | Gly:Lys:Arg 1.00:1.01:0.99 |
| 9 | MeO.CO—Lys($\epsilon$-Cbo)—Gly—Arg—pNA.AcOH $C_{32}H_{45}N_9O_{11}$ | 7 (10 mmoles) MeO.CO.Cl (12 mmoles) | Ex. 1e and 1f 82.0 | C 52.37 H 6.21 N 17.19 | 52.52 6.20 17.23 | Gly:Lys:Arg 1.00:1.00:0.98 |
| 10 | EtO.CO—Lys($\epsilon$-Cbo)—Gly—Arg—pNA.AcOH $C_{33}H_{47}N_9O_{11}$ | 7 (10 mmoles) EtO.CO.Cl (12 mmoles) | Ex. 1e and 1f 81.5 | C 53.00 H 6.42 N 17.14 | 53.15 6.35 16.90 | Gly:Lys:Arg 1.00:0.98:1.01 |
| 11 | isoBuO.CO—Lys($\epsilon$-Cbo)—Gly—Arg—pNA.AcOH $C_{35}H_{51}N_9O_{11}$ | 7 (10 mmoles) isoBuO.CO.Cl (12 mmoles) | Ex. 1e and 1f 79.6 | C 54.19 H 6.68 N 16.35 | 54.32 6.64 16.29 | Gly:Lys:Arg 1.00:1.01:1.01 |
| 12 | Propionyl—Lys($\epsilon$-Cbo)—Gly—Arg—pNA.AcOH $C_{33}H_{47}N_9O_{10}$ | 7 (10 mmoles) Propionyl anhydride (15 mmoles) | Ex. 1e and 1f 83.3 | C 54.12 H 6.54 N 17.40 | 54.31 6.49 17.27 | Gly:Lys:Arg 1.00:0.98:0.99 |
| 13 | Butyryl—Lys($\epsilon$-Cbo)—Gly—Arg—pNA.AcOH $C_{34}H_{49}N_9O_{10}$ | 7 (10 mmoles) Butyryl chloride (12 mmoles) | Ex. 1e and 1f 86.1 | C 54.81 H 6.67 N 17.17 | 54.90 6.64 16.95 | Gly:Lys:Arg 1.00:1.01:0.98 |
| 14 | EtO.CO.CH$_2$CO—Lys($\epsilon$-Cbo)—Gly—Arg—pNA.AcOH $C_{35}H_{49}N_9O_{12}$ | 7 (10 mmoles) EtO.CO.CH$_2$CO.Cl (12 mmoles) | Ex. 1e and 1f 76.4 | C 53.48 H 6.25 N 16.16 | 53.36 6.27 16.00 | Gly:Lys:Arg 1.00:1.00:1.02 |
| 15 | Suc—Lys($\epsilon$-Cbo)—Gly—Arg—pNA.AcOH $C_{34}H_{47}N_9O_{12}$ | 7 (10 mmoles) Succinyl anhydride (14 mmoles) | Ex. 1e and 1f 73.4 | C 52.59 H 6.18 N 16.33 | 52.77 6.12 16.29 | Gly:Lys: Arg 1.00:0.98:0.99 |

-continued

| Ex. | End products | Starting products | Method Yield % | Elementary analysis found % | calc. % | Amino acid analysis |
|---|---|---|---|---|---|---|
| 16 | Bz—Lys($\epsilon$-Cbo)—Gly—Arg—pNA.AcOH $C_{37}H_{47}N_9O_{10}$ | 7 (10 mmoles) Benzoic acid anhydride (15 mmoles) | Ex. 1e and 1f 84.7 | C 56.89 H 6.11 N 16.31 | 57.13 6.09 16.21 | Gly:Lys:Arg 1.00:1.00:0.98 |
| 17 | Tos—Lys($\epsilon$-Cbo)—Gly—Arg—pNA.AcOH $C_{37}H_{49}N_9O_{11}S$ | 7 (10 mmoles) Tosylchloride (12 mmoles) | Ex. 1e and 1f 85.2 | C 53.58 H 6.00 N 15.38 S 3.75 | 53.68 5.97 15.23 3.87 | Gly:Lys:Arg 1.00:0.97:1.01 |
| 18 | Caproyl—Lys($\epsilon$-Cbo)—Gly—Arg—pNA.AcOH $C_{36}H_{53}N_9O_{10}$ | 7 (10 mmoles) Caproyl—OpNP (11.5 mmoles) | Ex. 1e and 1f 84.9 | C 55.95 H 7.00 N 16.39 | 56.02 6.92 16.33 | Gly:Lys:Arg 1.00:0.99:0.99 |
| 19 | MeO—CO—$CH_2CH_2$—CO—Lys($\epsilon$-Cbo)—Gly—Arg—pNA.AcOH $C_{35}H_{49}N_9O_{12}$ | 7 (10 mmoles) MeO.CO.$CH_2$.$CH_2$.CO.Cl (12 mmoles) | Ex. 1e and 1f 83.8 | C 53.19 H 6.29 N 16.15 | 53.36 6.27 16.00 | Gly:Lys:Arg:$\beta$-Ala 1.00:0.98:0.98:0.95 |
| 20 | BOC—Gly—Lys($\epsilon$-Cbo)—Gly—Arg—pNA.AcOH $C_{37}H_{54}N_{10}O_{12}$ | 7 (10 mmoles) BOC—Gly—OpNP (11.5 mmoles) | Ex. 1e and 1f 80.6 | C 53.50 H 6.61 N 16.98 | 53.48 6.55 16.86 | Gly:Lys:Arg 2.00:0.99:0.98 |
| 21 | H—Gly—Lys($\epsilon$-Cbo)—Gly—Arg—pNA.2$CF_3$COOH $C_{34}H_{44}N_{10}O_{12}F_6$ | 20 (5 mmoles) $CF_3$COOH (10 ml) | Ex. 1d 93.4 | C 45.38 H 4.97 N 15.69 F 12.40 | 45.44 4.93 15.59 12.68 | Gly:Lys:Arg 2.00:0.99:0.97 |
| 22 | MeO.CO—Gly—Lys($\epsilon$-Cbo)—Gly—Arg—pNA.AcOH $C_{34}H_{48}N_{10}O_{12}$ | 21 (2 mmoles) MeO.CO.Cl (2.4 mmoles) | Ex. 1e and 1f 80.7 | C 51.68 H 6.16 N 17.95 | 51.77 6.13 17.76 | Gly:Lys:Arg 2.00:1.00:0.97 |
| 23 | Bz—Gly—Lys($\epsilon$-Cbo)—Gly—Arg—pNA.AcOH $C_{39}H_{50}N_{10}O_{11}$ | 21 (2 mmoles) Benzoic acid anhydride (3 mmoles) | Ex. 1e and 1f 83.5 | C 55.91 H 6.04 N 16.99 | 56.11 6.04 16.78 | Gly:Lys:Arg 2.00:0.98:0.98 |
| 24 | Propionyl—Gly—Lys($\epsilon$-Cbo)—Gly—Arg—pNA.AcOH $C_{35}H_{50}N_{10}O_{11}$ | 21 (2 mmoles) Propionyl anhydride (3 mmoles) | Ex. 1e and 1f 84.6 | C 53.28 H 6.43 N 18.02 | 53.43 6.41 17.80 | Gly:Lys:Arg 2.00:1.01:0.98 |
| 25 | EtO.CO—Gly—Lys($\epsilon$-Cbo)—Gly—Arg—pNA.AcOH $C_{35}H_{50}N_{10}O_{12}$ | 21 (2 mmoles) EtO.CO.Cl (2.4 mmoles) | Ex. 1e and 1f 83.1 | C 52.30 H 6.35 N 17.67 | 52.36 6.28 17.45 | Gly:Lys:Arg 2.00:0.99:0.98 |
| 26 | Cbo—Gly—Lys($\epsilon$-Cbo)—Gly—Arg—pNA.AcOH $C_{40}H_{52}N_{10}O_{12}$ | 7 (10 mmoles) Cbo—Gly—OpNP (11.5 mmoles) | Ex. 1e and 1f 80.9 | C 55.25 H 6.10 N 16.28 | 55.55 6.06 16.20 | Gly:Lys:Arg 2.00:1.01:0.99 |
| 27 | BOC—Lys($\epsilon$-Cbo)—Ala—Arg—pNA.AcOH $C_{36}H_{53}N_9O_{11}$ | 2HBr.H—Ala—Arg—pNA (10 mmoles) BOC—Lys($\epsilon$-Cbo)—OpNP (11.5 mmoles) | Ex. 1e and 1f 84.3 | C 54.66 H 6.82 N 16.20 | 54.88 6.78 16.00 | Ala:Lys:Arg 1.00:0.98:1.02 |
| 28 | H—Lys($\epsilon$-Cbo)—Ala—Arg—pNA.2$CF_3$COOH $C_{33}H_{43}N_9O_{11}F_6$ | 27 (10 mmoles) $CF_3$COOH (15 ml) | Ex. 1d 93.7 | C 46.20 H 5.11 N 14.96 F 13.15 | 46.32 5.06 14.73 13.32 | Ala:Lys:Arg 1.00:0.99:1.01 |
| 29 | Ac—Lys($\epsilon$-Cbo)—Ala—Arg—pNA.AcOH $C_{33}H_{47}N_9O_{10}$ | 28 (2 mmoles) $Ac_2O$ (3 mmoles) | Ex. 1e and 88.4 | C 54.08 H 6.56 | 54.31 6.49 | Ala:Lys:Arg 1.00:0.98:1.00 |
| 30 | MeO.CO—Lys($\epsilon$-Cbo)—Ala—Arg—pNA.AcOH $C_{33}H_{47}N_9O_{11}$ | 28 (2 mmoles) MeO.CO.Cl (2.4 mmoles) | Ex. 1e and 1f 86.0 | C 52.96 H 6.34 N 17.08 | 53.15 6.35 16.90 | Ala:Lys:Arg 1.00:1.01:0.99 |
| 31 | Bz—Lys($\epsilon$-Cbo)—Ala—Arg—pNA.AcOH $C_{38}H_{49}N_9O_{10}$ | 28 (2 mmoles) Benzoic acid anhydride (3 mmoles) | Ex. 1e and 1f 85.8 | C 57.50 H 6.25 N 16.03 | 57.64 6.24 15.92 | Ala:Lys:Arg 1.00:0.99:0.98 |
| 32 | $CH_3.SO_2$—Lys($\epsilon$-Cbo)—Ala—Arg—pNA.AcOH $C_{32}H_{47}N_9O_{11}S$ | 28 (2 mmoles) $CH_3.SO_2$.Cl (2.4 mmoles) | Ex. 1e and 1f 90.2 | C 49.96 H 6.25 N 16.60 S 4.05 | 50.19 6.19 16.46 4.19 | Ala:Lys:Arg 1.00:0.98:0.98 |
| 33 | BOC—$\beta$-Ala—Lys($\epsilon$-Cbo)—Gly—Arg—pNA.AcOH $C_{38}H_{56}N_{10}O_{12}$ | 7 (10 mmoles) BOC—$\beta$-Ala—OpNP (11.5 mmoles) | Ex. 1e and 1f 84.9 | C 53.85 H 6.73 N 16.66 | 54.02 6.68 16.58 | Gly:Lys:Arg:$\beta$-Ala 1.00:0.99:1.01:0.97 |
| 34 | H—$\beta$-Ala—Lys($\epsilon$-Cbo)—Gly—Arg—pNA.2$CF_3$COOH $C_{35}H_{46}N_{10}O_{12}F_6$ | 33 (5 mmoles) $CF_3$COOH (10 ml) | Ex. 1d 96.1 | C 45.84 H 5.12 N 15.50 F 12.45 | 46.05 5.08 15.35 12.49 | Gly:Lys:Arg:$\beta$-Ala 1.00:0.98:1.00:0.96 |
| 35 | Ac-$\beta$-Ala—Lys($\epsilon$-Cbo)—Gly—Arg—pNA.AcOH $C_{35}H_{50}N_{10}O_{11}$ | 34 (2 mmoles) $Ac_2O$ (3 mmoles) | Ex. 1e and 1f | C 53.40 H 6.48 N 17.75 | 53.43 6.41 17.80 | Gly:Lys:Arg:$\beta$-Ala 1.00:1.01:0.98:0.96 |

-continued

| Ex. | End products | Starting products | Method Yield % | Elementary analysis found % | calc. % | Amino acid analysis |
|---|---|---|---|---|---|---|
| 36 | MeO.CO—β-Ala—Lys(ε-Cbo)—Gly—Arg—pNA.AcOH C₃₅H₅₀N₁₀O₁₂ | 34 (2 mmoles) MeO.CO.Cl (2.4 mmoles) | 83.6 Ex. Ie and If 85.0 | C 52.46<br>H 6.29<br>N 17.58 | 52.36<br>6.28<br>17.45 | Gly:Lys:Arg:β-Ala 1.00:0.99:0.98:0.97 |
| 37 | Propionyl-β-Ala—Lys—(ε-Cbo)—Gly—Arg—pNA.AcOH C₃₆H₅₂N₁₀O₁₁ | 34 (2 mmoles) Propionyl anhydride (3 mmoles) | Ex. Ie and If 86.2 | C 54.00<br>H 6.63<br>N 17.55 | 53.99<br>6.54<br>17.49 | Gly:Lys:Arg:β-Ala 1.00:1.01:0.99:0.98 |
| 38 | EtO.CO-β-Ala—Lys(ε-Cbo)—Gly—Arg—pNA.AcOH C₃₆H₅₂N₁₀O₁₂ | 34 (2 mmoles) EtO.CO.Cl (2.4 mmoles) | Ex. Ie and If 84.5 | C 52.86<br>H 6.41<br>N 17.19 | 52.93<br>6.42<br>17.15 | Gly:Lys:Arg:β-Ala 1.00:1.01:0.98:0.96 |
| 39 | Bz—β-Ala—Lys(ε-Cbo)—Gly—Arg—pNA.AcOH C₄₀H₅₂N₁₀O₁₁ | 34 (2 mmoles) Benzoic acid anhydride (3 mmoles) | Ex. Ie and If 86.0 | C 56.30<br>H 6.15<br>N 16.65 | 56.59<br>6.17<br>16.50 | Gly:Lys:Arg:β-Ala 1.00:1.00:0.98:0.95 |
| 40 | BOC—Phe—Lys(ε-Cbo)—Gly—Arg—pNA.AcOH C₄₄H₆₀N₁₀O₁₂ | 7 (10 mmoles) BOC—Phe—OpNP (11.5 mmoles) | Ex. Ie and If 79.8 | C 57.10<br>H 6.66<br>N 15.34 | 57.38<br>6.57<br>15.21 | Gly:Lys:Arg:Phe 1.00:0.98:0.98:1.02 |
| 41 | H—Phe—Lys(ε-Cbo)—Gly—Arg—pNA.2CF₃COOH C₄₁H₅₀N₁₀O₁₂F₆ | 40 (5 mmoles) CF₃COOH (10 ml) | Ex. Id 94.7 | C 49.71<br>H 6.12<br>N 14.24<br>F 11.44 | 49.80<br>5.10<br>14.16<br>11.53 | Gly:Lys:Arg:Phe 1.00:0.99:1.01:0.99 |
| 42 | BOC—D-Phe—Lys(ε-Cbo)—Gly—Arg—pNA.AcOH C₄₄H₆₀N₁₀O₁₂ | 7 (10 mmoles) BOC—D-Phe—OpNP (11.5 mmoles) | Ex. Ie and If 82.9 | C 57.18<br>H 6.60<br>N 15.38 | 57.38<br>6.57<br>15.21 | Gly:Lys:Arg:D—Phe 1.00:1.01:0.98:1.01 |
| 43 | H—D-Phe—Lys(ε-Cbo)—Gly—Arg—pNA.2CF₃COOH C₄₁H₅₀N₁₀O₁₂F₆ | 42 (5 mmoles) CF₃COOH (10 ml) | Ex. Id 94.5 | C 49.66<br>H 5.11<br>N 14.32<br>F 11.39 | 49.80<br>5.10<br>14.16<br>11.53 | Gly:Lys:Arg:D-Phe 1.00:0.99:0.98:1.02 |
| 44 | BOC—CHA—Lys(ε-Cbo)—Gly—Arg—pNA.AcOH C₄₄H₆₆N₁₀O₁₂ | 7 (10 mmoles) BOC—CHA—OpNP (11.5 mmoles) | Ex. Ie and If 82.6 | C 56.82<br>H 7.23<br>N 15.25 | 57.00<br>7.18<br>15.11 | Gly:Lys:Arg:CHA 1.00:0.98:1.00:0.96 |
| 45 | H—CHA—Lys(ε-Cbo)—Gly—Arg—pNA.2CF₃COOH C₄₁H₅₆N₁₀O₁₂F₆ | 44 (5 mmoles) CF₃COOH (10 ml) | Ex. Id 93.1 | C 49.28<br>H 5.66<br>N 14.14<br>F 11.25 | 49.49<br>5.67<br>14.08<br>11.46 | Gly:Lys:Arg:CHA 1.00:1.01:0.98:0.95 |
| 46 | BOC—γ-But—Lys(ε-Cbo)—Gly—Arg—pNA.AcOH C₃₉H₅₈N₁₀O₁₂ | 7 (10 mmoles) BOC—γ-But—OpNP (11.5 mmoles) | Ex. Ie and If 81.7 | C 54.54<br>H 6.91<br>N 16.40 | 54.53<br>6.81<br>16.31 | Gly:Lys:Arg:γ-But 1.00:1.02:0.98:0.94 |
| 47 | H—γ-But—Lys(ε-Cbo)—Gly—Arg—pNA.2CF₃COOH C₃₆H₄₈N₁₀O₁₂F₆ | 46 (5 mmoles) Cf₃COOH (10 ml) | Ex. Id 92.9 | C 46.39<br>H 5.27<br>N 15.10<br>F 12.16 | 46.65<br>5.22<br>15.11<br>12.30 | Gly:Lys:Arg:γ-But 1.00:0.99:1.01:0.95 |
| 48 | BOC—Ph'Gly—Lys(ε-Cbo)—Gly—Arg—pNA.AcOH C₄₃H₅₈N₁₀O₁₂ | 7 (10 mmoles) BOC—Ph'Gly—OpNP (11.5 mmoles) | Ex. Ie and If 79.8 | C 56.80<br>H 6.48<br>N 15.62 | 56.94<br>6.45<br>15.44 | Gly:Lys:Arg:Ph'Gly 1.00:1.01:0.98:1.02 |
| 49 | H—Ph'Gly—Lys(ε-Cbo)—Gly—Arg—pNA.2CF₃COOH C₄₀H₄₈N₁₀O₁₂F₆ | 48 (5 mmoles) CF₃COOH (10 ml) | Ex. Id 92.9 | C 48.96<br>H 5.01<br>N 14.40<br>F 11.55 | 49.28<br>4.96<br>14.37<br>11.69 | Gly:Lys:Arg:Ph'Gly 1.00:1.01:0.98:0.99 |
| 50 | BOC—CHG—Lys(ε-Cbo)—Gly—Arg—pNA.AcOH C₄₃H₆₄N₁₀O₁₂ | 7 (10 mmoles) BOC—CHG—OpNP (11.5 mmoles) | Ex. Ie and If 83.4 | C 56.29<br>H 7.15<br>N 15.49 | 56.56<br>7.07<br>15.34 | Gly:Lys:Arg:CHG 1.00:1.02:1.00:0.97 |
| 51 | H—CHG—Lys(ε-Cbo)—Gly—Arg—pNA.2CF₃COOH C₄₀H₅₄N₁₀O₁₂F₆ | 50 (5 mmoles) CF₃COOH (10 ml) | Ex. Id 96.0 | C 48.86<br>H 5.60<br>N 14.21<br>F 11.60 | 48.98<br>5.55<br>14.28<br>11.62 | Gly:Lys:Arg:CHG 1.00:1.00:0.98:0.96 |
| 52 | BOC—D-CHG—Lys(ε-Cbo)—Gly—Arg—pNA.AcOH C₄₃H₆₄N₁₀O₁₂ | 7 (10 mmoles) BOC—D-CHG—OpNP | Ex. Ie and If | C 56.40<br>H 7.06<br>N 15.50 | 56.56<br>7.07<br>15.34 | Gly:Lys:Arg:D—CHG 1.00:0.98:0.97:0.94 |
| 53 | H—D-CHG—Lys(ε-Cbo)—Gly—Arg—pNA.2CF₃COOH C₄₀H₅₄N₁₀O₁₂F₆ | 52 (5 mmoles) CF₃COOH (10 ml) | Ex. Id 93.7 | C 49.11<br>H 5.63<br>N 14.38<br>F 11.48 | 48.98<br>5.55<br>14.28<br>11.62 | Gly:Lys:Arg:D—CHG 1.00:1.01:0.98:0.95 |
| 54 | BOC—CHT—Lys(ε-Cbo)—Gly—Arg—pNA.AcOH C₄₄H₆₆N₁₀O₁₃ | 7 (10 mmoles) BOC—CHT—OpNP (11.5 mmoles) | Ex. Ie and If 83.1 | C 55.79<br>H 7.11<br>N 15.09 | 56.04<br>7.05<br>14.85 | Gly:Lys:Arg:CHT 1.00:0.98:1.00:0.96 |
| 55 | H—CHT—Lys(ε-Cbo)—Gly—Arg—pNA.2CF₃COOH | 54 (5 mmoles) CF₃COOH (10 ml) | Ex. Id 93.6 | C 48.68<br>H 5.63<br>N 14.04 | 48.71<br>5.58<br>13.86 | Gly:Lys:Arg:CHT 1.00:1.00:0.97:0.97 |

-continued

| Ex. | End products | Starting products | Method Yield % | Elementary analysis found % | calc. % | Amino acid analysis |
|---|---|---|---|---|---|---|
| | $C_{41}H_{56}N_{10}O_{13}F_6$ | | | F 11.10 | 11.28 | |
| 56 | BOC—Lys($\epsilon$-4-MeO.Cbo)— Gly—Arg—pNA.AcOH $C_{36}H_{53}N_9O_{12}$ | Id (10 mmoles) BOC—Lys($\epsilon$-4-MeO.Cbo)—OpNP (11.5 mmoles) | Ex. Ie and If 76.8 | C 53.58 H 6.67 N 15.70 | 53.79 6.65 15.68 | Gly:Lys:Arg 1.00:0.98:0.99 |
| 57 | BOC—Lys($\epsilon$-4-Me.Cbo)— Gly—Arg—pNA.AcOH $C_{36}H_{53}N_9O_{11}$ | Id (10 mmoles) BOC—Lys($\epsilon$-4-Me.Cbo)—OpNP (11.5 mmoles) | Ex. Ie and If 79.5 | C 54.54 H 6.83 N 16.18 | 54.88 6.78 16.00 | Gly:Lys:Arg 1.00:0.99:0.98 |
| 58 | BOC—Lys($\epsilon$-4-Cl.Cbo)— Gly—Arg—pNA.AcOH $C_{35}H_{50}N_9O_{11}Cl$ | Id (10 mmoles) BOC—Lys($\epsilon$-4-Cl.Cbo)—OpNP (11.5 mmoles) | Ex. Ie and If 84.9 | C 51.83 H 6.25 N 15.76 Cl 4.48 | 52.01 6.24 15.60 4.39 | Gly:Lys:Arg 1.00:1.00:1.02 |
| 59 | H—Lys($\epsilon$-Cbo)—Gly— Arg—MCA—2CF$_3$COOH $C_{36}H_{44}N_8O_{11}F_6$ | 2e (5 mmoles) CF$_3$COOH (10 ml) | Ex. Id 68.5 | C 49.11 H 5.10 N 13.01 F 12.80 | 49.20 5.05 12.75 12.97 | Gly:Lys:Arg 1.00:1.01:0.98 |
| 60 | MeO.CO—Lys($\epsilon$-Cbo)— Gly—Arg—MCA.AcOH $C_{36}H_{48}N_8O_{11}$ | 59 (2 mmoles) MeO.CO.Cl (2.4 mmoles) | Ex. Ie and If 84.0 | C 56.05 H 6.33 N 14.69 | 56.24 6.29 14.58 | Gly:Lys:Arg 1.00:0.98:0.99 |
| 61 | H—Lys($\epsilon$-Cbo)—Gly— Arg—DPA. 2CF$_3$COOH $C_{36}H_{46}N_8O_{13}F_6$ | 3e (5 mmoles) CF$_3$COOH (10 ml) | Ex. Id 90.6 | C 47.49 H 5.15 N 12.36 F 12.40 | 47.37 5.08 12.28 12.49 | Gly:Lys:Arg 1.00:1.01:0.98 |
| 62 | Propionyl—Lys($\epsilon$-Cbo)— Gly—Arg—DPA.AcOH $C_{37}H_{52}N_8O_{12}$ | 61 (2 mmoles) Propionyl anhydride (3 mmoles) | Ex. Ie and If 84.3 | C 55.22 H 6.58 N 14.18 | 55.49 6.54 13.99 | Gly:Lys:Arg 1.00:0.98:0.97 |
| 63 | EtO.CO—Lys($\epsilon$-Cbo)— Gly—Arg—DPA.AcOH $C_{37}H_{52}N_8O_{13}$ | 61 (2 mmoles) EtO.CO.Cl (2.4 mmoles) | Ex. Ie and If 84.8 | C 54.20 H 6.51 N 13.96 | 54.40 6.42 13.72 | Gly:Lys:Arg 1.00:1.01:0.99 |

The following Table comprises numerical values relating to the rate at which the peptide derivatives of the invention are split by $C_1$-esterase. The listed values were determined as follows: 0.2 ml of a $2\times10^{-3}$-molar peptide derivative solution was added at 37° to a mixture consisting of 1.8 ml of trisimidazole buffer and 0.015 ml of a solution containing 800 tosyltyrosine ethyl ester units (TTEU) of $C_1$-esterase per ml. Then, the increase in the optical density $\Delta OD$ which was caused by the split product (e.g. p-nitroaniline, 4-methoxy-2-naphthylamine or 4-methyl-7-amino-coumarin) formed as a result of the splitting of the peptide derivative within a period of 5 min. was measured at 405 nm. In the case of fluorescent split products (e.g. 1- or 2-naphthylamine or 1,3-di(methoxycarbonyl)-5-aminobenzene) the increase in the optical density was measured at the corresponding emission wave length. Based on the determined values in the increase of the optical density per time unit and the molar extinction coefficient the amount of the split product formed per time unit was calculated in nanomoles.

TABLE

| Peptide derivative | Splitting rate | Peptide derivative | Splitting rate |
|---|---|---|---|
| 1 | 2.97 | 2 | 2.50 |
| 3 | 2.60 | 4 | 2.33 |
| 5 | 2.50 | 6 | 2.27 |
| 7 | 2.97 | 8 | 5.27 |
| 9 | 7.27 | 10 | 6.47 |
| 11 | 5.87 | 12 | 5.60 |
| 13 | 4.93 | 14 | 4.13 |
| 15 | 2.57 | 16 | 2.67 |
| 17 | 1.00 | 18 | 3.67 |
| 19 | 4.13 | 20 | 9.50 |
| 21 | 5.90 | 22 | 8.00 |
| 23 | 9.97 | 24 | 7.63 |
| 25 | 6.50 | 26 | 2.10 |
| 27 | 2.93 | 28 | 2.83 |
| 29 | 3.57 | 30 | 4.63 |
| 31 | 2.67 | 32 | 1.87 |
| 33 | 3.67 | 34 | 4.00 |
| 35 | 4.60 | 36 | 5.80 |
| 37 | 5.13 | 38 | 6.40 |
| 39 | 9.53 | 40 | 1.00 |
| 41 | 10.50 | 42 | 0.67 |
| 43 | 4.90 | 44 | 0.67 |
| 45 | 3.30 | 46 | 3.17 |
| 47 | 4.50 | 48 | 1.00 |
| 49 | 7.27 | 50 | 0.83 |
| 51 | 3.70 | 52 | 0.67 |
| 53 | 1.00 | 54 | 0.50 |
| 55 | 3.30 | 56 | 3.10 |
| 57 | 3.17 | 58 | 2.83 |
| 59 | 2.33 | 60 | 5.83 |
| 61 | 2.67 | 62 | 5.00 |
| 63 | 5.67 | | |

The splitting rate is expressed in nanomoles of split product formed per minute by 1 TTEU of $C_1$-esterase.

The assaying of the $C_1$-esterase inhibitor level in blood plasma can be carried out as follows: A mixture of 1.6 ml of trisimidazole buffer having a pH of 7.4 and anionic strength of 0.2 and 0.1 ml of citrated plasma is incubated together with 0.1 ml of purified $C_1$-esterase during 4 min. at 37°. To the incubate 0.2 ml of a $2\times10^{-3}$-molar aqueous solution of a substrate according to the invention is added. If the substrate carries a p-nitroanilino group as the chromogenic group ($R^1$), the quantity of the split product p-nitroaniline ($R^1$-H) released per minute is measured spectrophotometrically at 405 nm. In a test system which contains no plasma but otherwise has the same composition the quantity of p-nitroaniline released per minute is measured in the same manner. The $C_1$-esterase inhibitor level of the blood plasma is determined from the difference between the two measured values.

I claim:

1. Peptide derivatives of formula:

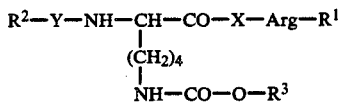

wherein $R^1$ is a chromogenic amino group which is substituted with an aromatic or heterocyclic radical and which is capable of being split off by enzymatic hydrolysis with formation of a colored or fluorescent compound;

$R^2$ is hydrogen,
a straight or branched alkanoyl group having 2 to 6 carbon atoms,
a cyclohexylcarbonyl group,
an $\omega$-carboxyl, $\omega$-methoxycarbonyl or $\omega$-ethoxycarbonyl-alkanoyl group having 2 to 4 carbon atoms in the alkanoyl group,
a straight or branched alkoxycarbonyl group having 1 to 4 carbon atoms in the alkoxy group,
an alkylsulfonyl group having 1 to 2 carbon atoms in the alkyl group, a phenyl- or p-toluyl-sulfonyl group,
an unsubstituted or substituted benzoyl group, or
a benzyloxycarbonyl group the nucleus of which is unsubstituted or substituted;

$R^3$ is a benzyl group the nucleus of which is unsubstituted or substituted;

X is a glycyl or alanyl group; and

Y is a single bond or a group of formula

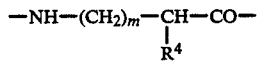

wherein $R^4$ is a benzyl, phenyl, cyclohexyl, cyclohexylmethyl, 4-hydroxybenzyl or 4-hydroxycyclohexylmethyl group and m is zero, the amino acid represented by Y having L- or D-configuration; or hydrogen and m is zero, 1 or 2; and salts thereof with mineral or organic acids.

2. Peptide derivatives according to claim 1 in which $R^1$ is a p-nitrophenylamino, 1- or 2-naphthylamino, 4-methoxy-2-naphthylamino, 4-methyl-7-coumarylamino or 1,3-di(methoxycarbonyl)-phen-5-yl-amino group.

3. Peptide derivatives according to claim 2 in which $R^3$ is a benzyl, 4-methylbenzyl, 4-methoxybenzyl or 2-, 3- or 4-chlorobenzyl group.

4. Peptide derivatives according to claim 1 in which $R^2$ is an alkanoyl group having 2 to 6 carbon atoms or an alkoxycarbonyl group having 1 to 4 carbon atoms in the alkoxy group, Y is a single bond and $R^3$ is a benzyl group.

5. Peptide derivatives according to claim 1 which include BOC-Lys($\epsilon$-Cbo)-Gly-Arg-pNA.AcOH, 2AcOH.H-Lys($\epsilon$-Cbo)-Gly-Arg-pNA, Ac-Lys($\epsilon$-Cbo)-Gly-Arg-pNA.AcOH, $CH_3OCO$-Lys($\epsilon$-Cbo)-Gly-Arg-pNA.AcOH, $C_2H_5OCO$-Lys($\epsilon$-Cbo)-Gly-Arg-pNA.AcOH, isoBuOCO-Lys($\epsilon$-Cbo)-Gly-Arg-pNA.AcOH, $CH_3CH_2CO$-Lys($\epsilon$-Cbo)-Gly-Arg-pNA.AcOH, $CH_3(CH_2)_2CO$-Lys($\epsilon$-Cbo)-Gly-Arg-pNA.AcOH, $CH_3CH_2OCO$-$CH_2$-CO-Lys($\epsilon$-Cbo)-Gly-Arg-pNA.AcOH, BOC-Lys($\epsilon$-Cbo)-Ala-Arg-pNA.AcOH, H-Lys($\epsilon$-Cbo)-Ala-Arg-pNA.2CF$_3$COOH, Ac-Lys($\epsilon$-Cbo)-Ala-Arg-pNA.AcOH, $CH_3O$-CO-Lys($\epsilon$-Cbo)-Ala-Arg-pNA.AcOH, BOC-Gly-Lys($\epsilon$-Cbo)-Gly-Arg-pNA.AcOH, 2CF$_3$COOH.H-Gly-Lys($\epsilon$-Cbo)-Gly-Arg-pNA, $CH_3O$-CO-Gly-Lys($\epsilon$-Cbo)-Gly-Arg-pNA.AcOH and $CH_3$-$CH_2$-CO-Gly-Lys($\epsilon$-Cbo)-Gly-Arg-pNA.AcOH.

6. Peptide derivatives according to claim 1 in which $R^3$ is a benzyl, 4-methylbenzyl, 4-methoxybenzyl or 2-, 3- or 4-chlorobenzyl group.

7. A method for quantitatively assaying $C_1$-esterase enzyme in a medium containing same, which method comprises:

(a) reacting a medium which contains $C_1$-esterase proenzyme or in which the latter is formed or consumed with peptide derivatives of the formula:

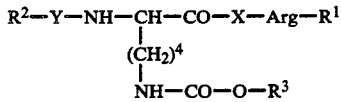

wherein $R^1$ is a chromogenic amino group which is substituted with an aromatic or heterocyclic radical and which is capable of being split off by enzymatic hydrolysis with formation of a colored or fluorescent compound;

$R^2$ is hydrogen,
a straight of branched alkanoyl group having 2 to 6 carbon atoms;
a cyclohexylcarbonyl group;
an $\omega$-carboxyl, $\omega$-methoxycarbonyl or $\omega$-ethoxycarbonly-alkanoyl group having 2 to 4 carbon atoms in the alkanoyl group;
a straight or branched alkoxycarbonyl group having 1 to 4 carbon atoms in the alkoxy group;
an alkylsulfonyl group having 1 to 2 carbon atoms in the alkyl group;
a phenyl- or p-toluyl-sulfonyl group;
an unsubstituted or substituted benzoyl group; or
a benzyloxycarbonyl group the nucleus of which is unsubstituted or substituted;

X is a glycyl or alanyl group; and

Y is a single bond or a group of formula

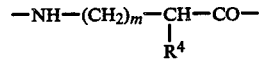

wherein
$R^4$ is a benzyl, phenyl, cyclohexyl, cyclohexylmethyl, 4-hydroxybenzyl or 4-hydroxycyclohexylmethyl group and m is zero, the amino acid represented by Y having L- or D-configuration; or hydrogen and m is zero, 1, or 2; and salts thereof with mineral or organic acids;

(b) splitting the product $R^1$-H by catalytic hydrolytic action of the enzyme on the peptide derivative; and (c) measuring the quantity of split product $R^1$-H released per unit time.

8. The method of claim 7 wherein the quantity of split product $R^1$-H is measured by photometric, spectrophotometric, fluorescence-spectrophotometric, or electrochemical means.

9. The method of claim 7 wherein the medium is human blood plasma.

* * * * *